United States Patent
Ozaki et al.

(10) Patent No.: US 6,547,530 B2
(45) Date of Patent: Apr. 15, 2003

(54) FLUID PUMP APPARATUS

(75) Inventors: Takayoshi Ozaki, Iwata (JP); Minoru Suzuki, Iwata (JP)

(73) Assignees: NTN Corporation, Osaka (JP); Terumo Kabushiki Kaisha, Tokyo (JP)

( * ) Notice: Subject to any disclaimer, the term of this patent is extended or adjusted under 35 U.S.C. 154(b) by 30 days.

(21) Appl. No.: 09/855,744

(22) Filed: May 16, 2001

(65) Prior Publication Data

US 2002/0009363 A1 Jan. 24, 2002

(30) Foreign Application Priority Data

May 19, 2000 (JP) ........................................ 2000-148127
May 19, 2000 (JP) ........................................ 2000-148128

(51) Int. Cl.⁷ ......................... F04B 49/06; F04B 17/00; A61M 1/00; F03B 13/00
(52) U.S. Cl. .................... 417/44.1; 417/366; 417/423.7; 417/423.12; 604/151; 415/900
(58) Field of Search ................... 417/44.1, 366, 417/423.7, 423.12; 604/151; 415/900

(56) References Cited

U.S. PATENT DOCUMENTS

| | | | | |
|---|---|---|---|---|
| 4,688,998 A | * | 8/1987 | Olsen et al. | 417/356 |
| 5,385,581 A | * | 1/1995 | Bramm et al. | 417/356 |
| 6,015,275 A | * | 1/2000 | Suzuki et al. | 310/90.5 |
| 6,129,660 A | * | 10/2000 | Nakazeki et al. | 415/900 |
| 6,227,817 B1 | * | 5/2001 | Paden | 417/356 |

FOREIGN PATENT DOCUMENTS

| | | | |
|---|---|---|---|
| JP | 9-303283 | * | 11/1997 |
| JP | 2001-182683 | * | 7/2001 |

* cited by examiner

Primary Examiner—Charles G. Freay
Assistant Examiner—Michael K. Gray
(74) Attorney, Agent, or Firm—McDermott, Will & Emery

(57) ABSTRACT

There is provided a fluid pump wherein in a casing at a pump unit there is provided an impeller coupled with a rotor contactless and also supported contactless by a controlled magnetic bearing unit, and rotated by a motor to output a fluid, with a position detection unit, an electromagnet or a motor stator cooled by a fluid flowing through a pump chamber.

17 Claims, 14 Drawing Sheets

FLUID PUMP APPARATUS

BACKGROUND OF THE INVENTION

1. Field of the Invention

The present invention relates to fluid pump apparatus and more specifically to those for use for example for artificial hearts, employing a magnetic bearing to magnetically levitate an impeller to deliver fluid such as blood.

2. Description of the Background Art

FIG. 15 is a vertical cross section of one example of a body of a blood pump as one example of a conventional fluid pump apparatus. In FIG. 15, the pump body includes a cylindrical housing 1 internally partitioned axially by partitions 11, 12, 13 and 14 to accommodate an electromagnet unit 20, a pump unit 30 and a motor unit 40. Electromagnet unit 20 has an electromagnet 21 and a magnetic bearing sensor 22 incorporated therein. Casing 1 has on the electromagnet unit 20 side (or one side) a side wall having a center provided with an inlet 15 introducing blood. At least three electromagnets 21 and at least three magnetic bearing sensors 22 surround inlet 15 circumferentially. Electromagnets 21 and magnetic bearing sensors 22 are attached to an internal wall surface of partition 11 externally isolating electromagnet unit 20.

In pump unit 30 an impeller 31 is rotatably housed and it has a portion closer to electromagnet unit 20 that is supported by electromagnet unit 21 contactless through partition 12, and magnetic bearing sensor 22 senses the distance between magnetic bearing sensor 22 and one side of impeller 31. Impeller 31 has the other side with a plurality of permanent magnets 32 buried therein circumferentially.

Motor unit 40 houses a motor stator 41 and motor rotor 42. Motor stator 41 is arranged on an external peripheral surface of a cylindrical member 43 extending cylindrically from an internal wall surface of partition 14 externally partitioning motor unit 40. Motor rotor 42 rotates around a shaft supported by an internal peripheral surface of cylindrical member 43 via a motor bearing 44 provided in the form of a ball or roller bearing. Motor rotor 42 has an inner peripheral surface provided with a permanent magnet 47 facing an electromagnet 46 of motor stator 41 and motor rotor 42 rotates through their magnetic force, borne by motor bearing 44. Motor rotor 42 has a surface facing pump unit 30 and having a plurality of permanent magnets 45 buried therein circumferentially, opposite to permanent magnet 32 buried in impeller 31, through partition 13.

In the blood pump apparatus thus configured, magnetic bearing sensor 22 provides an output which is referred to by a controller 10, described hereinafter, to control a current flowing to electromagnet 21, to control an attractive force provided by electromagnet 21 toward the opposite side of impeller 31.

Furthermore impeller 31 has a portion closer to motor unit 40 that is affected by the attractive force introduced by permanent magnets 32 and 45. And impeller 31 is magnetically levitated by a non-controlled bearing provided by permanent magnets 32 and 45 and a controlled bearing provided by electromagnet 21. Impeller 31 is rotated by a driving force of motor unit 40 and blood introduced through inlet 15 is output through an outlet (not shown) formed at pump unit 30.

In the FIG. 15 fluid pump apparatus, electromagnet 21 generates heat attributed to a current flowing to magnetically levitate impeller 31 and motor stator 41 generates heat attributed to a current flowing to rotate motor rotor 42. Furthermore, motor bearing 44 is provided for example in the form of a ball or roller bearing and generates heat through friction as motor rotor 42 rotates. Furthermore, to externally release the heat generated by electromagnet 21, electromagnet 21 and magnetic bearing sensor 22 are fixed on an internal wall surface of partition 11 provided in contact with an outside of casing 1, and motor stator 41 is also provided at an internal wall surface of partition 14 provided in contact with an outside of casing 1, at an external peripheral surface of cylindrical member 43. Thus casing 1 is increased in temperature by the heat generated by electromagnet 21 and motor stator 41.

When the heat increases temperature, the heat is transferred to magnetic bearing sensor 22 and the sensor consequently has a temperature drift, which disadvantageously results in unreliable sensing.

Furthermore if fluid pump apparatus in FIG. 15 is used for example as a blood pump and thus configures a portion of an artificial heart and implanted in a human body the heat generated as described above may have a negatively effect on the tissues of the human body. This needs to be addressed by an approach taken separately. Such approaches to be taken, however, would increase the blood pump in size. Thus it is impossible to reduce the blood pump for the artificial heart in size or weight.

FIG. 16 is a block diagram showing a controller driving the conventional fluid pump apparatus shown in FIG. 15.

In FIG. 16, controller 10 includes a sequence circuit 101 externally receiving a control signal corresponding to commands for rotation, levitation and the like, an AC-DC converter 102 receiving an AC power supply, and a monitor circuit 103 monitoring the blood pump's operation and externally communicating the condition. AC-DC converter 102 converts an AC voltage to a DC voltage which is in turn applied to a motor power amplifier 104, a magnetic bearing power amplifier 124 and a DC-DC converter 105. DC-DC converter 105 stabilizes the DC voltage and supplies it to a circuit as described hereinafter.

Controller 10 also includes a sensor circuit 110 having a carrier wave generation circuit 111, a tuning circuit 112 and an amplifier 113 incorporated therein. Carrier wave generation circuit 111 generates a carrier wave which is in turn provided via a connector 150 to magnetic bearing sensor 22 housed in housing 1 of the pump body. Magnetic bearing sensor 22, as shown in FIG. 15, outputs a signal having an amplitude corresponding to a distance between magnetic bearing sensor 22 and impeller 31. Tuning circuit 112 is tuned in to the signal to extract a detection signal, amplifier 113 amplifies the detection signal and provides it to magnetic bearing control circuit 121.

A magnetic bearing control circuit 121 receives the detection signal, responsively provides PID control, and feeds the control output to a magnetic bearing PWM circuit 122. Magnetic bearing PWM circuit 122 uses pulse width modulation (PWM) to vary the received control signal in pulse width. A magnetic bearing gate drive circuit 123 is operative to control a magnetic bearing power amplifier 124 to drive electromagnet 21.

Furthermore, a motor control circuit 131 outputs to a motor PWM circuit 132 a control signal based on a command input to sequence circuit 101. Motor PWM circuit 132 outputs a PWMed control signal to a motor gate drive circuit 133. Motor gate drive circuit 133 outputs a drive signal to motor power amplifier 104. In response to the drive signal, motor power amplifier 104 drives motor stator 41.

In the blood pump apparatus shown in FIGS. 15 and 16, magnetic bearing sensor 22 has characteristics slightly varying to reflect a difference of an individual blood pump from another individual one. As such, in sensor circuit 110 an adjustment needs to be made for each sensor. As such, controller 10 is not compatible with each blood pump, which is a bottleneck in mass production.

Furthermore, magnetic bearing power amplifier 124, motor power amplifier 104 and the like generate significant heat attributed to switching-loss and controller 10 would also generate heat, which can have a negative effect on a human body when the apparatus is implanted therein.

SUMMARY OF THE INVENTION

Therefore a main object of the present invention is to provide a fluid pump apparatus reduced in size and weight and capable of efficiently release heat.

Another object of the present invention is to provide a fluid pump apparatus capable of providing compatibility between the pump body and the controller and also using blood to cool a heated portion thereof.

The present invention provides a fluid pump apparatus including: a pump unit having in a casing a rotative member rotated to output a fluid; a drive unit coupled with one side of the rotative member contactless through a magnetic force to levitate one side of the rotative member while rotatably driving one side of the rotative member; a position detection unit detecting a position of the rotative member in levitation; and a controlled magnetic bearing unit contactlessly supporting the other side of the rotative member in response to an output of the position detection unit, wherein heat generated at least one of the rotative member, the position detection unit and the controlled magnetic bearing unit is released via a fluid flowing through the pump unit.

Thus in accordance with the present invention if a position detection unit receiving a sensor output to determine the position of the impeller in levitation is housed in the casing the position detection unit can have characteristics adjusted to correspond to the sensor of the body of the fluid pump to maintain compatibility with a controller.

Furthermore, if any of a drive circuit controlling the drive unit or a magnetic bearing control circuit controlling the controlled magnetic bearing unit is housed in the casing then heat generated from the drive circuit can be efficiently cooled by a fluid to prevent the controller body from generating significant heat.

Preferably, the casing includes a first partition provided between the pump unit and the drive unit and a second partition provided between the pump unit and the controlled magnetic bearing unit, and the drive unit is attached to the first partition and the controlled magnetic bearing unit is attached to the second partition.

More preferably the position detection unit is attached to the second partition.

Still more preferably, the rotative member is formed in a disk having a side facing the drive unit and provided with a permanent magnet arranged circumferentially and the rotative member and the drive unit are coupled contactless through magnetic-coupling.

Still more preferably, the rotative member is formed in a disk having a side facing the drive unit and provided with a first permanent magnet arranged circumferentially, the drive unit is provided with a second permanent magnet arranged circumferentially to face the first permanent magnet, and the first and second permanent magnets provide magnetic-coupling to couple the rotative member and the drive unit together contactlessly.

Still more preferably the controlled magnetic bearing unit includes a plurality of electromagnets each configured of a magnetic pole, a yoke and a coil and having an S magnetic pole and an N magnetic pole with at least the yoke and coil arranged circumferentially.

Still more preferably the drive unit includes a motor stator and a motor rotor rotated by a magnetic force of the motor stator, the motor stator being attached to the second partition.

Still more preferably the pump unit has an internal surface coated with an antithrombotic substance such as heparin.

The present invention in another aspect provides a fluid pump having a casing, an impeller driven, levitated, a drive unit driving the impeller, a sensor sensing a position of the impeller in levitation, and a controlled magnetic bearing unit contactlessly supporting the impeller in response to an output of the sensor, wherein the casing has housed therein at least one of the following circuits. The position detection circuit operative in response to the output of the sensor to determine the position of the impeller in levitation, the drive circuit controlling the drive unit, and the magnetic bearing control circuit controlling the controlled magnetic bearing.

If the position detection circuit is housed in the casing the position detection circuit can be adjusted to correspond to characteristics of the incorporated sensor and thus maintain compatibility with a controller. If the drive circuit or the magnetic bearing control circuit is housed in the casing, heat generated from the circuits can be cooled with a fluid flowing into the pump.

Preferably the fluid pump further includes an alternating current to direct current conversion circuit converting an alternating-current voltage to a direct-current voltage, and a direct current to direct current conversion circuit converting the converted direct-current voltage to a different direct-current voltage, wherein the direct current to direct current conversion circuit is housed in the casing. In this example also heat generated at the direct current to direct current conversion circuit can be cooled by a fluid.

More preferably the fluid pump apparatus further includes: a carrier wave generation circuit generating a carrier wave; and a tuning circuit detecting a signal of the sensor tuned in to the carrier wave generated by the carrier wave generation circuit, to detect the position of the impeller in levitation, wherein the carrier wave generation circuit and the tuning circuit are housed in the casing. As such, by adjusting the carrier wave generation circuit and the tuning circuit to correspond to the sensor's characteristics, compatibility with a controller can be achieved.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
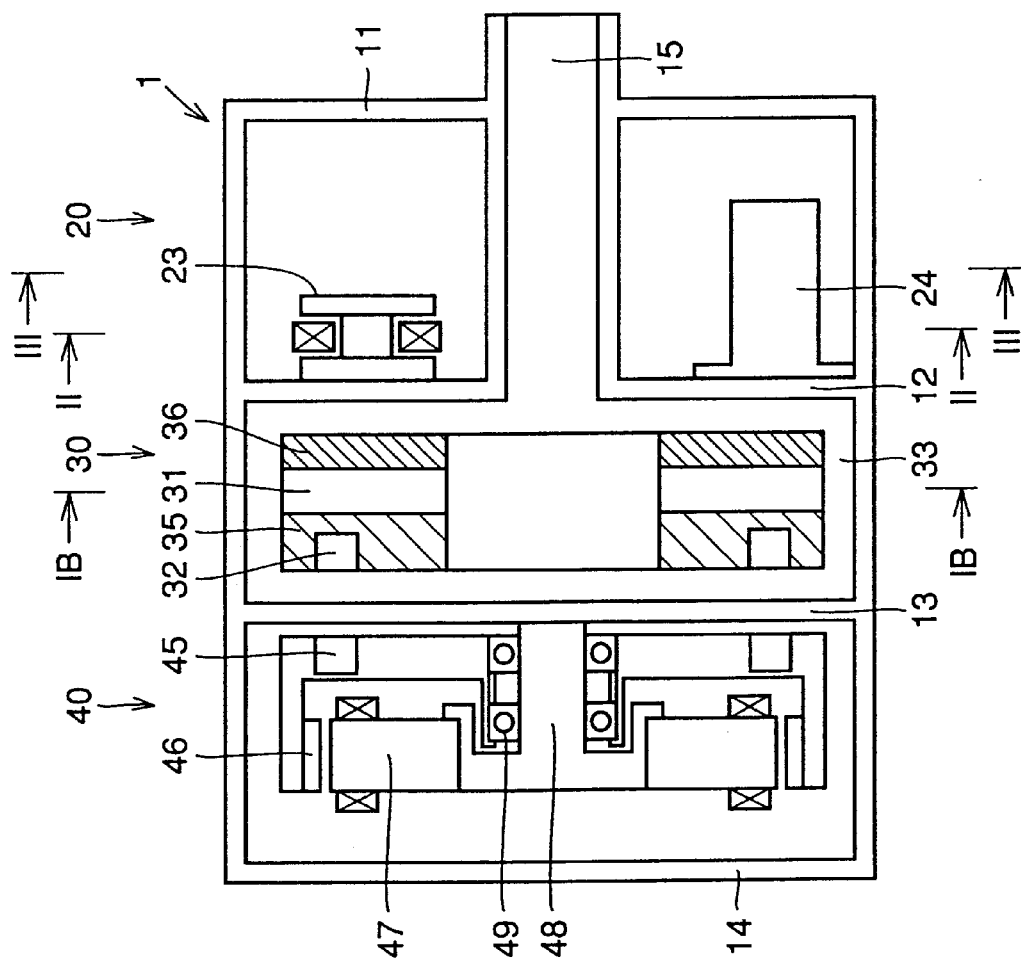
FIG. 1A is a vertical cross section of one embodiment of the present invention and FIG. 1B is a cross section thereof taken along line IB—IB of FIG. 1A.
Figure 2:
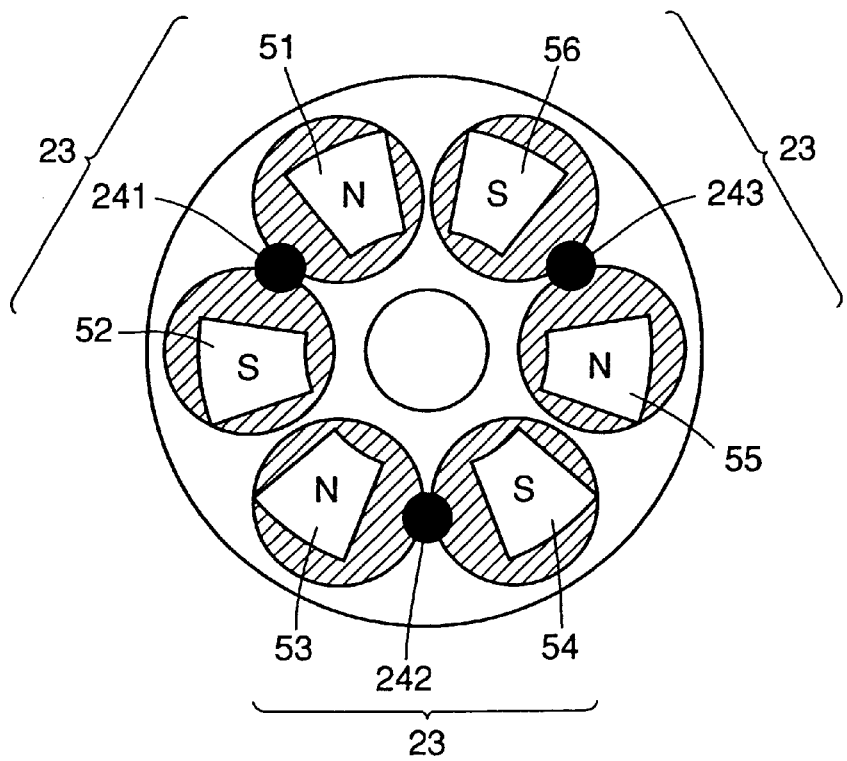
FIG. 2 is a cross section taken along line II—II of FIG. 1A.
Figure 3:
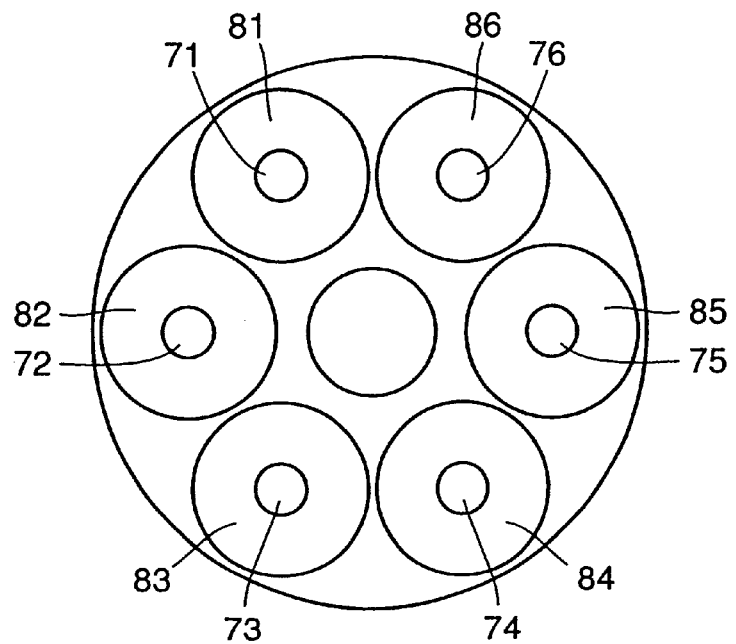
FIG. 3 is a cross section taken along line III—III of FIG. 1A.

FIGS. 1A and 1B show a fluid pump apparatus of one embodiment of the present invention. More specifically, FIG. 1A is a vertical cross section thereof and FIG. 1B is a cross section thereof taken along line IB—IB of FIG. 1A. FIG. 2 is a cross section taken along line II—II of FIG. 1A and FIG. 3 is a cross section taken along line III—III of FIG. 1A.

Figure 15:
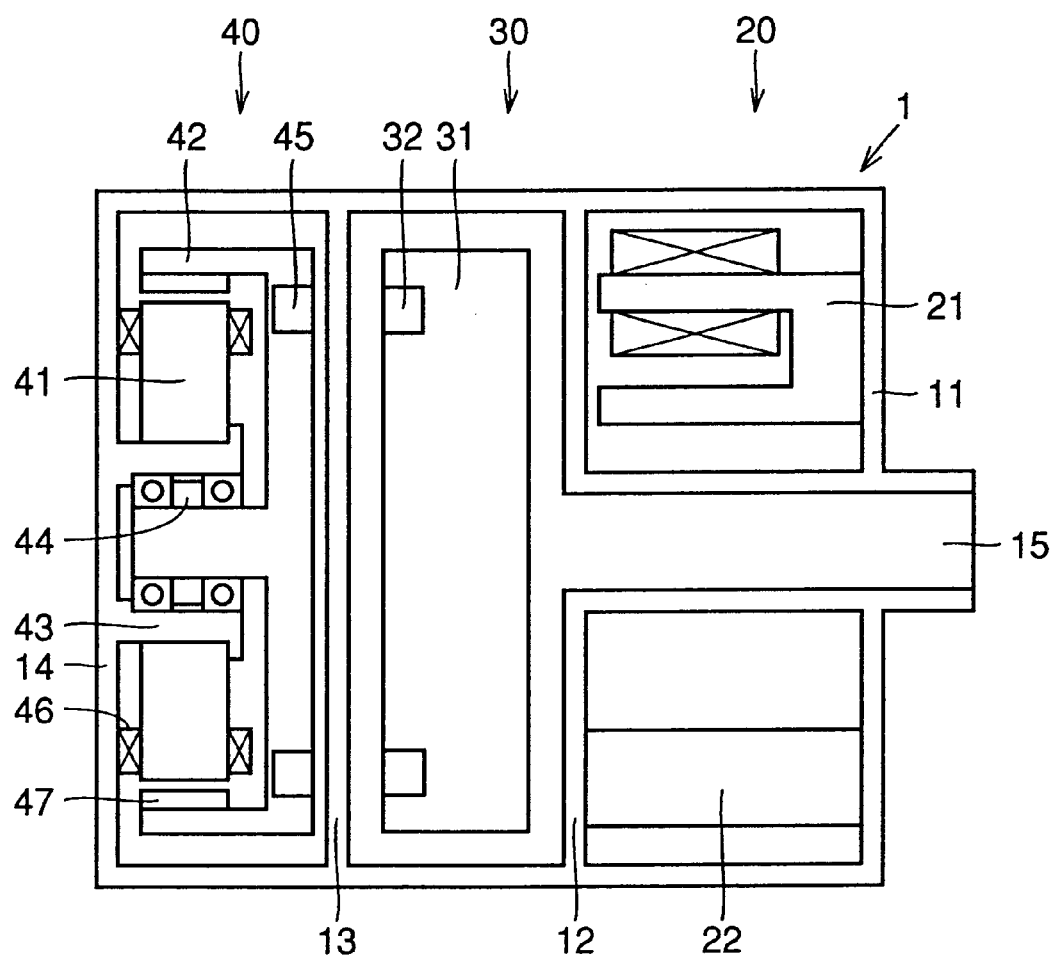
FIG. 15 is a vertical cross section of a body of a conventional blood pump.

In the FIG. 15, aforementioned conventional example, electromagnet 21 is attached to an internal wall surface of partition 11 provided in contact with an outside of casing 1 and motor stator 31 is also attached to an internal wall surface of partition 14 provided in contact with an outside of casing 1. In the FIG. 1A embodiment, by contrast, they are attached to wall surfaces of partitions 12 and 13 separating pump unit 30 and a fluid flowing through pump chamber 33, such as blood, cools electromagnet 21 and motor stator 31.

More specifically, the fluid pump apparatus includes a cylindrical casing 1 axially partitioned by partitions 11, 12, 13 and 14 to have sections housing a magnetic bearing unit 20, a pump unit 30 and a motor unit 40, respectively. Casing 1 is formed for example of plastic, ceramic, metal or the like, although of casing 1, partition 12 provided between magnetic bearing unit 20 and pump unit 30 and partition 13 provided between pump unit 30 and motor unit 40 are not allowed to be formed of magnetic material. Therefore they are accordingly formed of non-magnetic material.

At pump unit 30 casing 1 is internally provided with a pump chamber 33 in which an impeller 31 rotates to output a fluid through an outlet 16 (FIG. 1B). Impeller 31 has a plurality of vanes 34 spirally provided, as shown in FIG. 1B. Impeller 31 includes a non-magnetic member 35 having a permanent magnet configuring a non-controlled magnetic bearing and a soft magnetic member 36 corresponding to a rotor of a controlled magnetic bearing. Permanent magnet 32 is divided in a circumferential direction of impeller 31 and adjacent magnets are magnetized to have opposite magnetic poles.

Note that by coating the entire interior of pump chamber 33 with heparin or a similarly antithrombotic substance serving as an anticoagulant, formation of thrombus can be prevented therein and the fluid pump apparatus can thus be used as a blood delivering pump. In this example, the antithrombotic coating can effectively limit activation of coagulation system, protect platelets, limit activation, activation of inflammation system, activation of fibrinolysis system, and the like.

In FIGS. 1A and 1B, non-magnetic member 35 and soft magnetic member 36 are shown hatched. If the pump is used to deliver a corrosive fluid such as blood, the soft magnetic material is preferably a highly corrosive-resistant, ferritic stainless steel (SUS447J1, SUS444 or the like) and the non-magnetic material is preferably a highly corrosive-resistant, austenitic stainless steel (SUS316L or the like) or titanium alloy, pure titanium or the like.

Opposite to a side of impeller 31 having permanent magnet 32, a cylindrical member 48 is provided in motor unit 40, extending from a center of partition 13 toward partition 14. Cylindrical member 48 has an external peripheral surface provided with a motor bearing 49 provided in the form of a ball and roller bearing which supports motor rotor 46 rotatably. Cylindrical member 48 has an end with a motor stator 47 attached thereto. Motor rotor 46 is driven by motor stator 47 to rotate. Motor rotator 46 is circumferentially provided with the same number of permanent magnets 45 as permanent magnets 32 of impeller 31 opposite thereto to provide attractive force. Adjacent permanent magnets 45 are magnetized to have opposite magnetic poles.

Note that while the motor is a synchronous motor including a DC brushless motor, a non-synchronous motor including an induction motor, or the like, it may be any kind of motor.

Provided in electromagnet unit 20 are an electromagnet 23 and a magnetic bearing sensor 24, attached on a wall of partition 12 provided between electromagnet unit 20 and pump unit 30, opposite to that side of impeller 31 having soft magnetic member 36. Electromagnet 23 and magnetic bearing sensor 24 allow impeller 31 to be held at the center of pump chamber 33, matching the attractive force produced between permanent magnets 32 and 45.

Thus the heat generated at electromagnet 23 can be transferred to partition 12 and thus cooled by a fluid existing in pump unit 30. Similarly, the heat generated at motor stator 47 is also transferred through cylindrical member 48 to partition 13 and thus cooled by the fluid existing in motor unit 30. This can reduce heat transfer to outside casing 1 and also reduce heat transfer to magnetic bearing sensor 24 to provide a reliable sensing operation. Furthermore, if partitions 12 and 13 are increased in thickness to have a level of strength allowing electromagnet 23, magnetic bearing sensor 24 and motor stator 47 to be attached thereto, housing 1 can advantageously have an outer-diameter portion reduced in thickness.

Electromagnet 23 and magnetic bearing sensor 24 are arranged, as shown in FIGS. 2 and 3. More specifically, a plurality of paired, circumferentially arranged electromagnets 23 have magnetic poles 51 and 52 with a sensor 241 arranged therebetween, magnetic poles 53 and 54 with a sensor 242 arranged therebetween, and magnetic poles 55 and 56 with a sensor 243 arranged therebetween. Sensors 241 to 243 are typically a magnetic sensor, such as an eddy-current sensor, a reluctance sensor or the like.

Furthermore, as shown in FIG. 3, electromagnets 23 have their respective yokes 71–76 in the form of a column circumferentially arranged with electromagnet coils 81–86 wound therearound, respectively.

Circumferentially arranging magnetic poles 51–56 can increase the space housing electromagnet coils 81–86 that can be housed in magnetic bearing unit 40. This ensures a large space for winding the coils without increasing the size of the pump. Increasing a space for housing a coil in turn allows an electromagnet coil to have an increased turn count and an increased wire diameter and can thus save power for the electromagnet.

Furthermore, electromagnet yokes 71–76 in the form of a column can facilitate winding electromagnet coils 81–86 around electromagnet yokes 71–76, respectively. Electromagnet yokes 71–76 having a simple geometry ensures insulation from electromagnet coils 81–86. While electromagnet yokes 71–76 are cylindrical, they may be in the form of a prism, which can facilitate winding coils and thus ensuring an insulation withstand voltage between the coils and the yokes.

Furthermore while in FIGS. 2 and 3 electromagnet yokes 71–76 and electromagnet coils 81–86 are all arranged in a single circle, they may not be thus arranged if required to effectively ensure a space for housing the same.

With the magnetic bearing having each electromagnet with its magnetic pole and yoke arranged circumferentially, the magnetic bearing unit is not required to have a large space and the electromagnet yoke can also be provided in a cylinder or a prism to facilitate winding the coil and consequently ensuring an insulation withstand voltage between the coil and the yoke.

Figure 4:
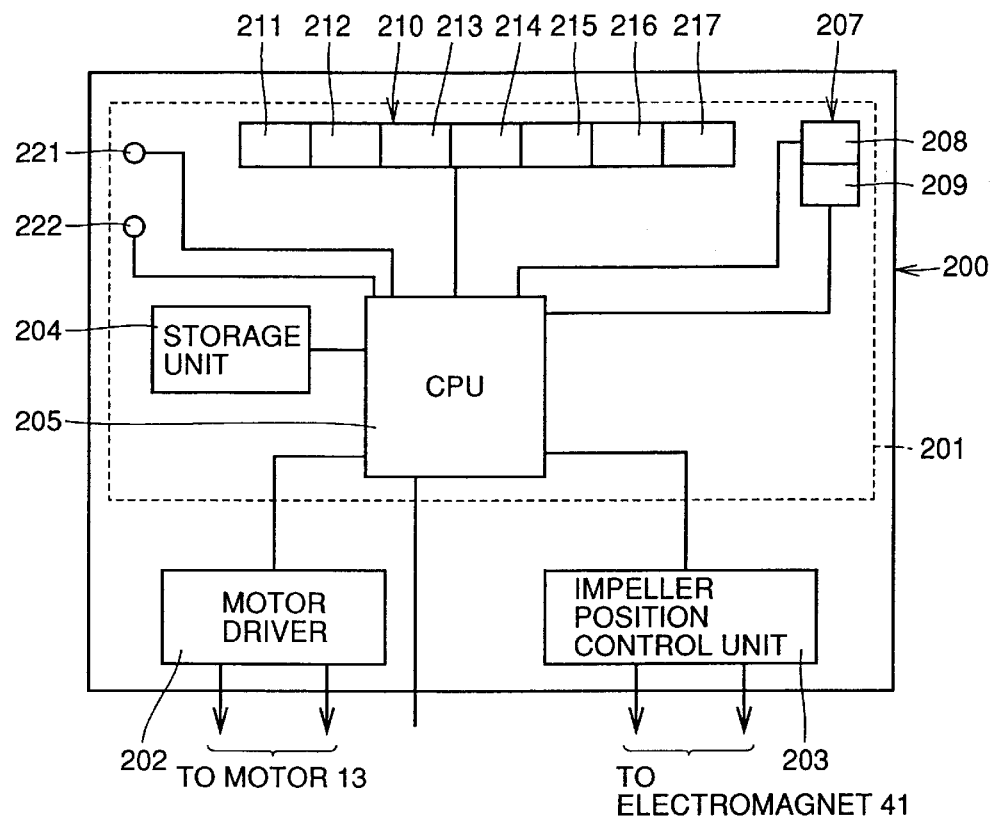
FIG. 4 is a block diagram showing a controller controlling a fluid pump apparatus of the present invention.

FIG. 4 is a block diagram showing a first embodiment of a controller for driving a magnetically levitated (maglev) pump in one embodiment of the present invention. In FIG. 4, a controller 200 includes a function provided to control the position of the impeller, a function provided to control the running torque of the impeller, a function using the impeller position control function to change the position of impeller 31 levitating in pump chamber 33, a function provided to measure the current of motor unit 40, and a function provided to calculate a viscosity of a fluid from a variation in current in motor unit 40 that is introduced when the function controlling the position of the impeller in levitation is operated to change the position of impeller 31 in levitation.

More specifically, controller 200 includes a controller body 201, a motor driver 202 and a control unit 203 provided to control the impeller's position. Motor driver 202 is provided to rotate motor unit 40, outputting a level of voltage corresponding to a motor rotation rate output from controller body 201. Control unit 203 maintains the impeller position in levitation output from controller body 201, controlling either one or both of a current flowing through and a voltage applied to electromagnet 23.

Magnetic bearing sensor 24 provides an output which is in turn input to control unit 203 to control a current flowing through electromagnet 23 to control the impeller 31 translation along its center axis (an axis z) and the impeller 31 rotation around axes x and y orthogonal to the center axis (axis z). Note that the output from magnetic bearing sensor 24 may be input to controller body 201 which is adapted to in turn output a voltage or current value applied to electromagnet 23.

Controller body 201 includes a storage unit (ROM) 204, a CPU 205, a display unit 210, and an input unit 207. Display unit 210 includes a set flow rate (SFR) display unit 211, a real flow rate (RFR) unit 212, a set pressure (SP) display unit 213, a real pressure (RP) display unit 214, a fluid temperature (FT) display unit 215, a fluid viscosity (FV) display unit 216, and an impeller speed (IS) display unit 217.

Furthermore, input unit 207 includes an SFR input unit 208 and an SP input unit 209.

Controller body 201 includes a data storage unit storing data of a relationship between fluid viscosity and motor current valiance, corresponding to a previously obtained relationship between fluid viscosity and motor current valiance depending on positional variance of the impeller in levitation (variance in motor drive current), or a relationship expression calculated from the data related to such relationship (for example data of a correlation expression or data of an expression of viscosity calculation), and the function provided for calculation of fluid viscosity calculates fluid viscosity from the data stored in storage unit 24 and the valiance of the current through motor unit 40 obtained when the impeller 23 position in levitation is changed via the function controlling the impeller position in levitation.

In other words, controller body 201 at storage unit 204 stores data related to a relationship between fluid viscosity and motor current variance corresponding to a previously obtained relationship between fluid viscosity and motor current variance depending on positional change of the impeller in levitation, or correlation data calculated from the data related to such relationship (also serving as data of an expression for viscosity calculation).

Figure 5:
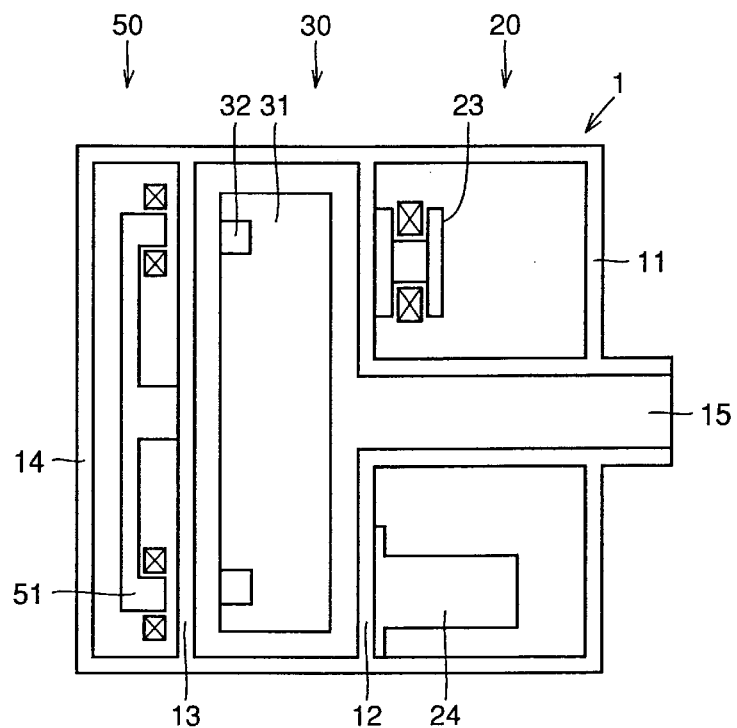
FIG. 5 is a vertical cross section of another embodiment of the present invention.

FIG. 5 is a vertical cross section of a fluid pump in another embodiment of the present invention. The present embodiment differs from the FIG. 1A embodiment only in a motor unit 50, and the embodiments are identical in electromagnet unit 20 and pump unit 30 and will thus not be described repeatedly.

In the FIG. 1A embodiment, motor unit 40 includes motor stator 47 provided with a coil and motor rotor 47 provided with a permanent magnet and arranged closer to pump unit 30. In the FIG. 5 embodiment, in contrast, a motor stator 51 is provided with a coil which cooperates with permanent magnet 32 of impeller 31 to provide a magnetic force to rotate impeller 31.

In the present embodiment, motor stator 51, generating heat, is also attached to partition 13 so that the heat of motor stator 51 can be cooled by a fluid existing in pump unit 30.

Figure 6:
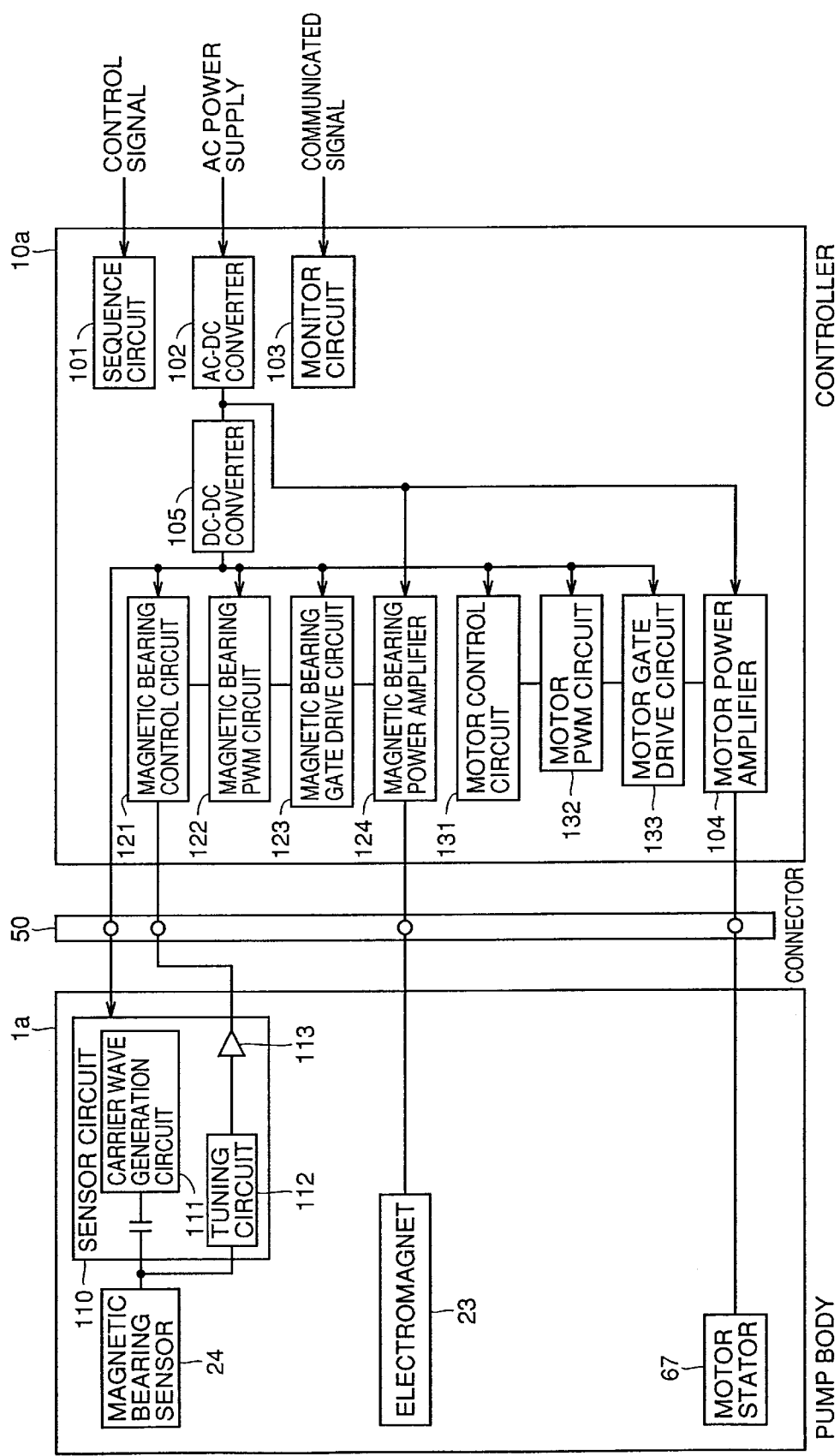
FIGS. 6–14 are block diagrams showing second to tenth embodiments of the controller of the present invention.
Figure 16:
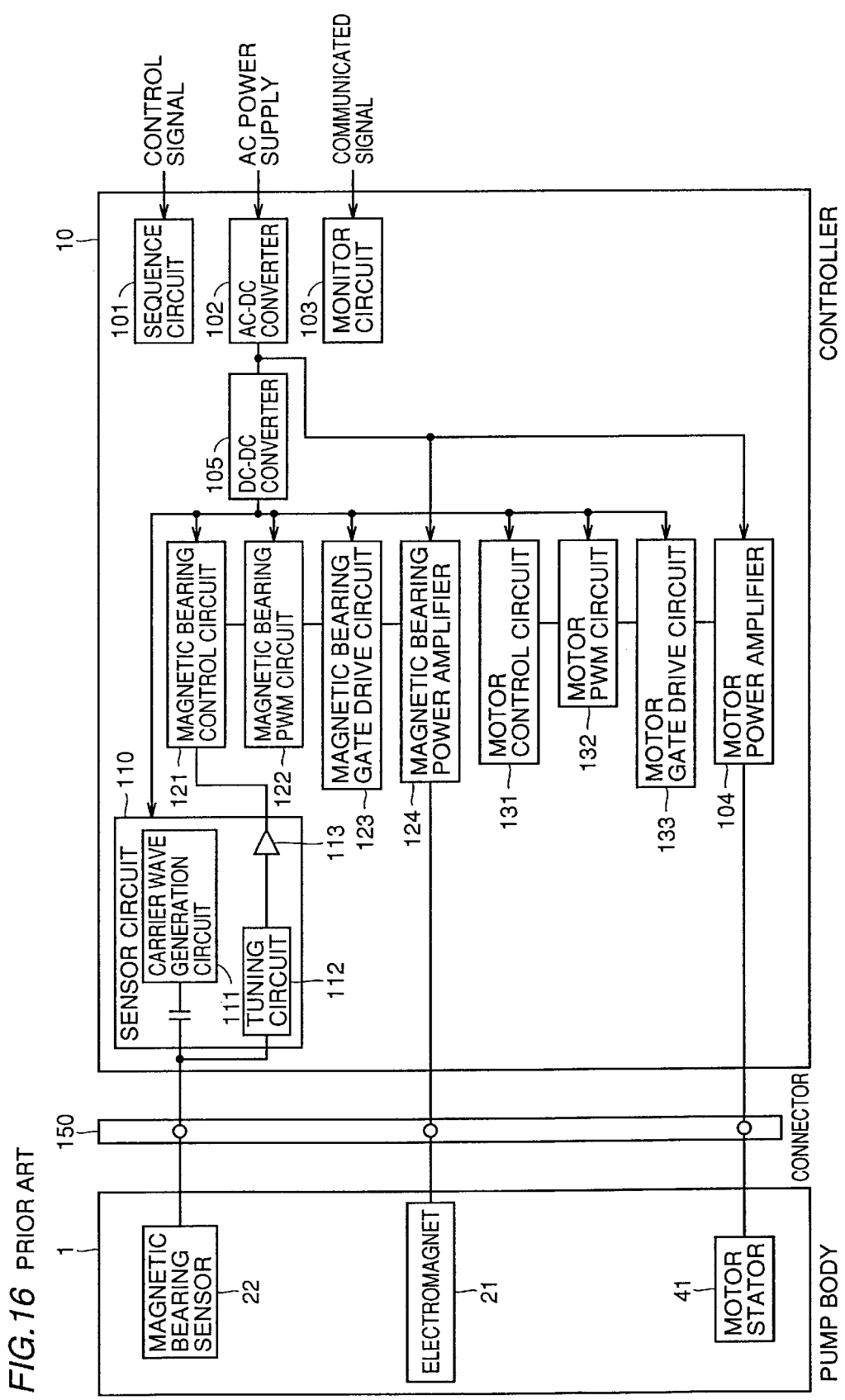
FIG. 16 is a block diagram showing a controller driving a conventional fluid pump.

FIG. 6 is a block diagram showing a second embodiment of the controller in accordance with the present invention. In the present embodiment, sensor circuit 110 is accommodated in a pump body 1a. A DC voltage is supplied from a controller 10a via a connector 50 to sensor circuit 110. Sensor circuit 110 provides an output which is in turn input via connector 50 to magnetic bearing control circuit 121. Sensor circuit 110 is configured including carrier wave generation circuit 111, tuning circuit 112 and amplifier 113, as shown in FIG. 16.

Controller 10a includes sequence circuit 101 receiving an external control signal including commands for rotation, levitation and the like, AC-DC converter 102 receiving an AC power supply, and monitor circuit 103 monitoring the blood pump's operation to externally communicate the condition thereof. Controller 10a also includes motor power amplifier 104, magnetic bearing power amplifier 124 and DC-DC converter 105 all receiving a direct-current power supply from AC-DC converter 102. Controller 10a also includes magnetic bearing PWM circuit 122, magnetic bearing gate drive circuit 123, motor control circuit 131, motor PWM circuit 132, and motor gate drive circuit 133. These circuits operate and are connected as has been previously described with reference to FIG. 16 and will thus not be described repeatedly.

In the FIG. 6 embodiment, sensor circuit 110, housed in pump body 1a, can be adjusted to correspond to magnetic bearing sensor 24, which allows compatibility with controller 10a.

In the third to tenth embodiments described hereinafter, the circuits denoted by the same reference characters as in FIG. 16 operate and are connected in the same manners as described and shown in the figure and they will thus not be described repeatedly. Only the circuits incorporated in pump bodies 1b–1i will be described and the other circuits incorporated in controllers 10b–10i will not be described.

Figure 7:
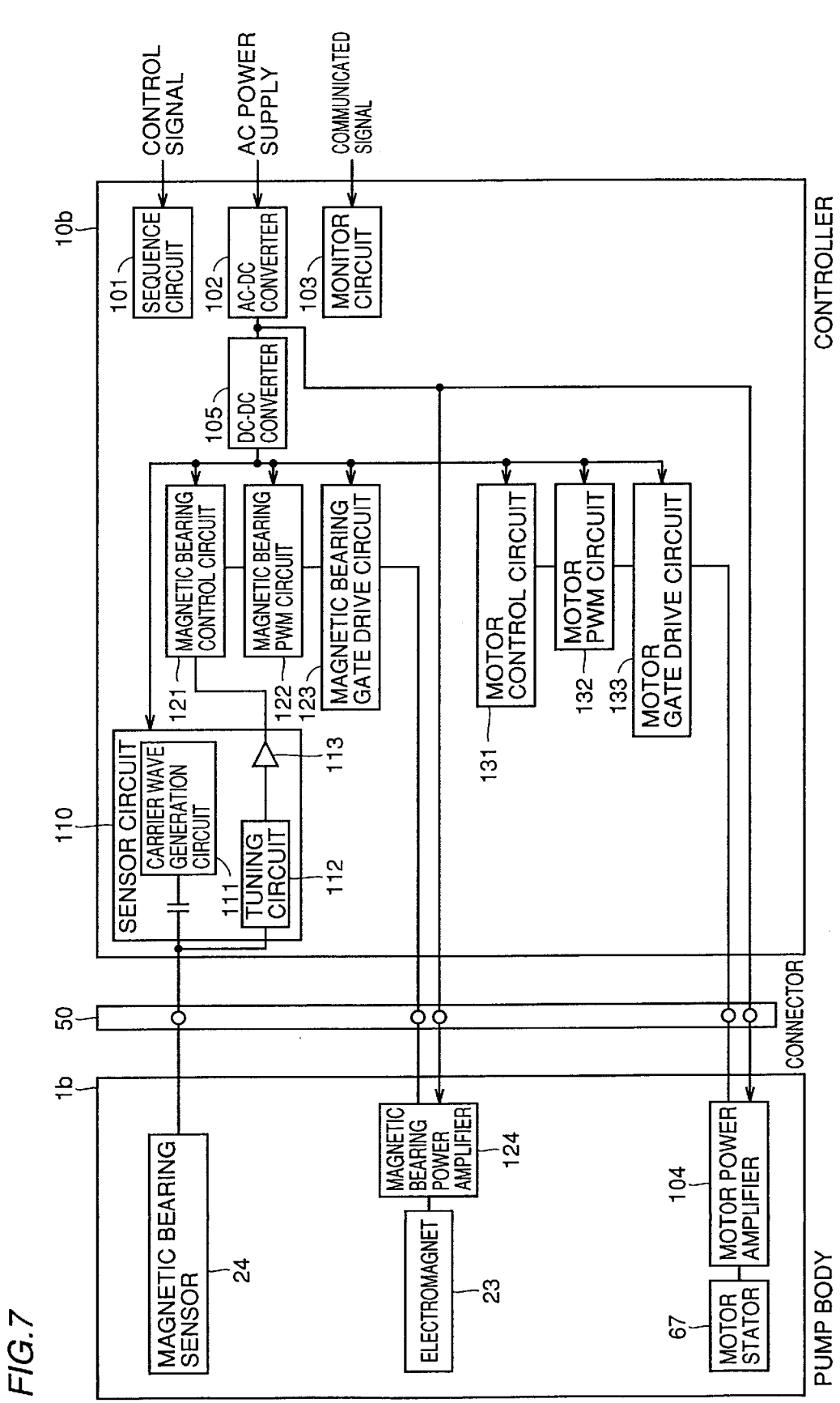

FIG. 7 shows a third embodiment of the controller in accordance with the present invention. In the present embodiment, magnetic bearing power amplifier 124 and motor power amplifier 104, both generating significant heat attributed to switching-loss, are incorporated in pump body 1b. In this example, magnetic bearing power amplifier 124 and motor power amplifier 104 also receive a direct-current voltage from AC-DC converter 102 provided in controller 10b, via connector 50.

In the present embodiment, magnetic bearing power amplifier 124 and motor power amplifier 104 that are incorporated in pump body 1b can have their heat cooled by blood delivered by pump body 1b. This can prevent controller 10b from generating significant heat.

Note that in the FIG. 7 embodiment pump body 1b may have incorporated therein not only magnetic bearing power amplifier 124 and motor power amplifier 104 but also a sensor circuit 110, as shown in FIG. 1A. Advantageously this can not only prevent controller 10b from generating significant heat but provide compatibility between pump body 1b and controller 10b.

Figure 8:
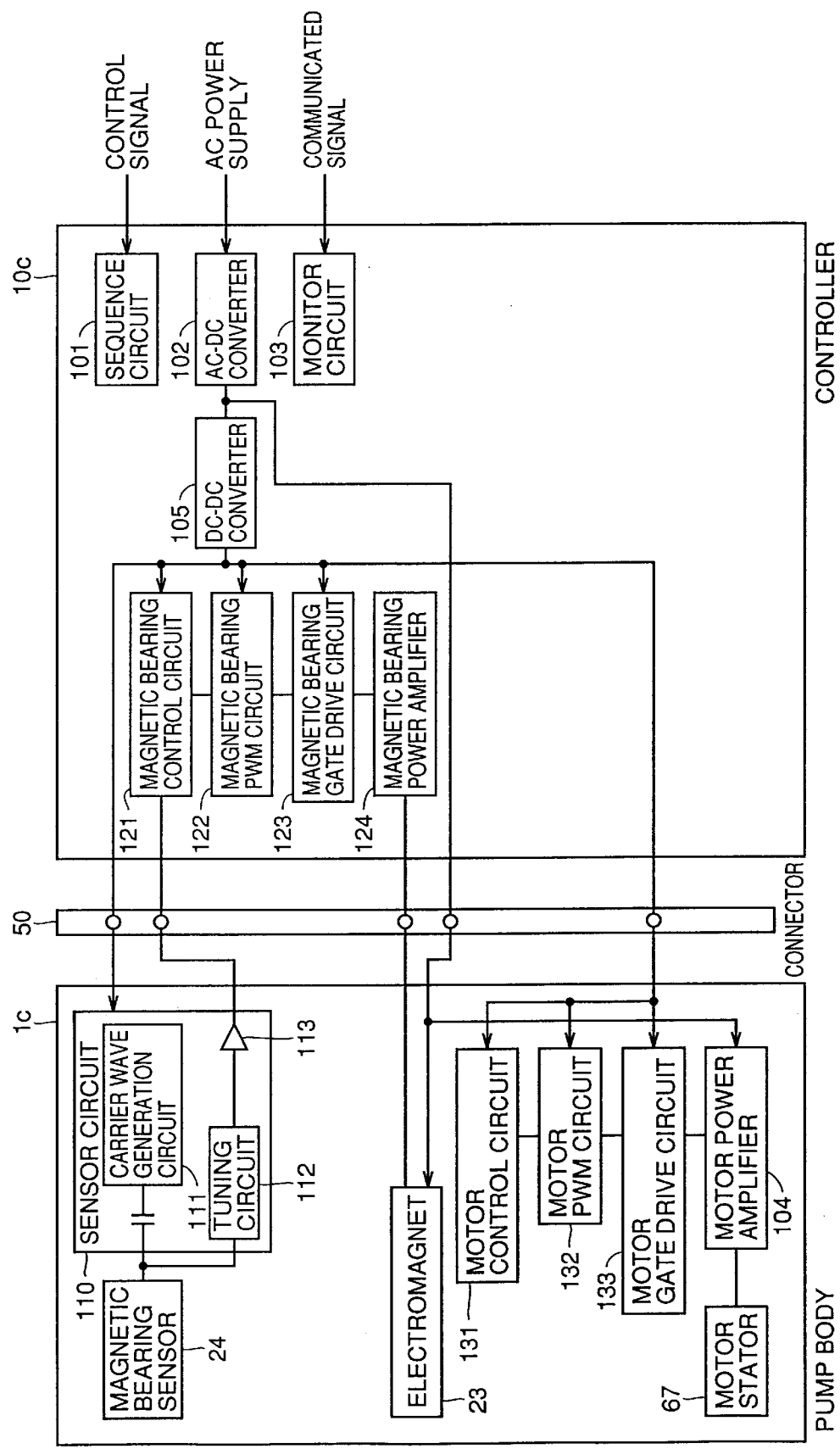

FIG. 8 is a block diagram showing a fourth embodiment of the controller in accordance with the present invention. In the present embodiment, a pump body 1c has incorporated therein sensor circuit 110, motor control circuit 131, motor PWM circuit 132, motor gate drive circuit 133 and motor power amplifier 104. Controller 10c is provided with the remaining configuration.

In the present embodiment, pump body 1c has sensor circuit 110 incorporated therein to have compatibility with controller 10c and pump body 1c also only have a motor-related configuration incorporated therein to prevent the body from having a large size.

Figure 9:
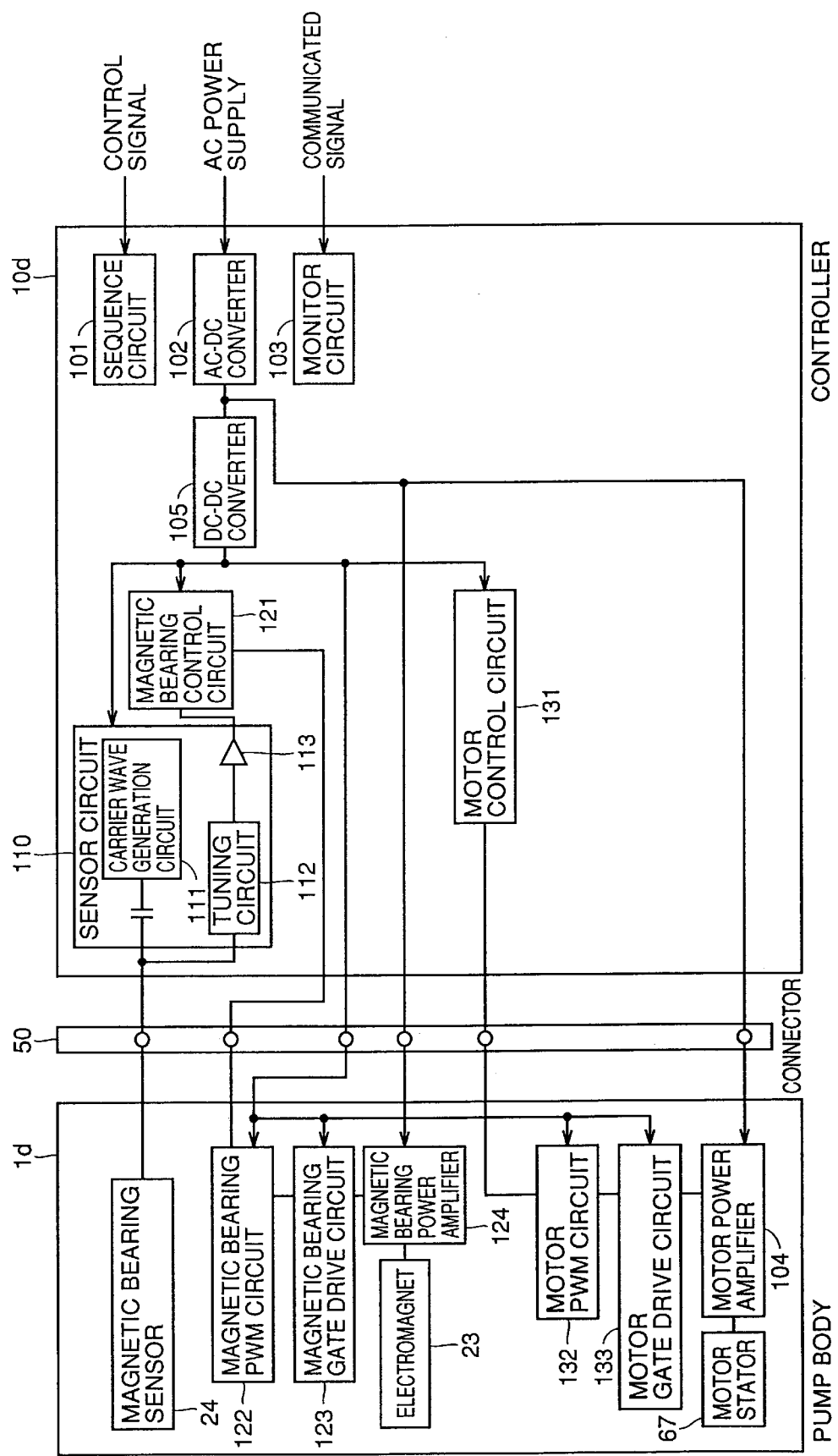

FIG. 9 is a block diagram showing a fifth embodiment of the controller in accordance with the present invention. In the present embodiment, a pump body 1d has incorporated therein magnetic bearing PWM circuit 122, magnetic bearing gate drive circuit 123 and magnetic bearing power amplifier 124 provided to control electromagnet 23 (hereinafter these three circuits will generally be referred to as a system driving electromagnet 23) and also has incorporated therein motor PWM circuit 132, motor gate drive circuit 133 and motor power amplifier 104 provided to control motor stator 41 (hereinafter these three circuits will generally be referred to as a system driving motor stator 67).

In the present embodiment a circuit portion dealing with a switching signal, such as magnetic bearing PWM circuit 122 and motor PWM circuit 132, can be incorporated in pump body 1d. As such, electromagnet 23, motor stator 67 and their driving systems can be less distant from each other to as a result provide a control signal free of significantly impaired quality and significant distortion: Such an impaired or distorted control signal would result in heat generation, which can be limited in the present embodiment. Furthermore, controller 10d has incorporated therein sensor circuit 110, magnetic bearing control circuit 121, motor control circuit 131 and the like.

Figure 10:
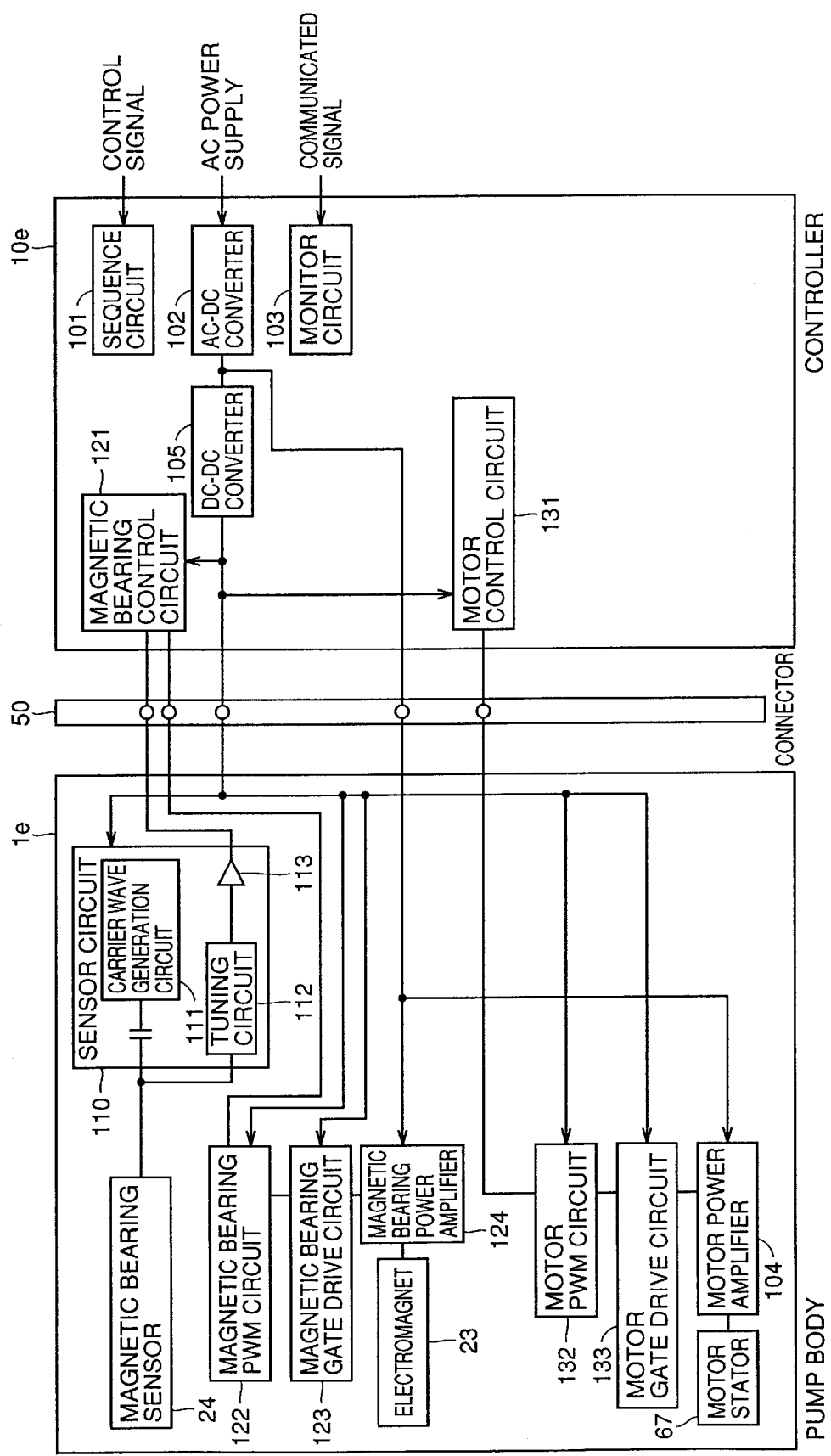

FIG. 10 is a block diagram showing a sixth embodiment of the controller in accordance with the present invention. The present embodiment is the FIG. 4 embodiment plus the FIG. 1A embodiment, not only the electromagnet 23 and motor stator 67 driving systems but also sensor circuit 110 incorporated in a pump body 1e, to achieve a combination of the effects of the FIGS. 6 and 9 embodiments.

Figure 11:
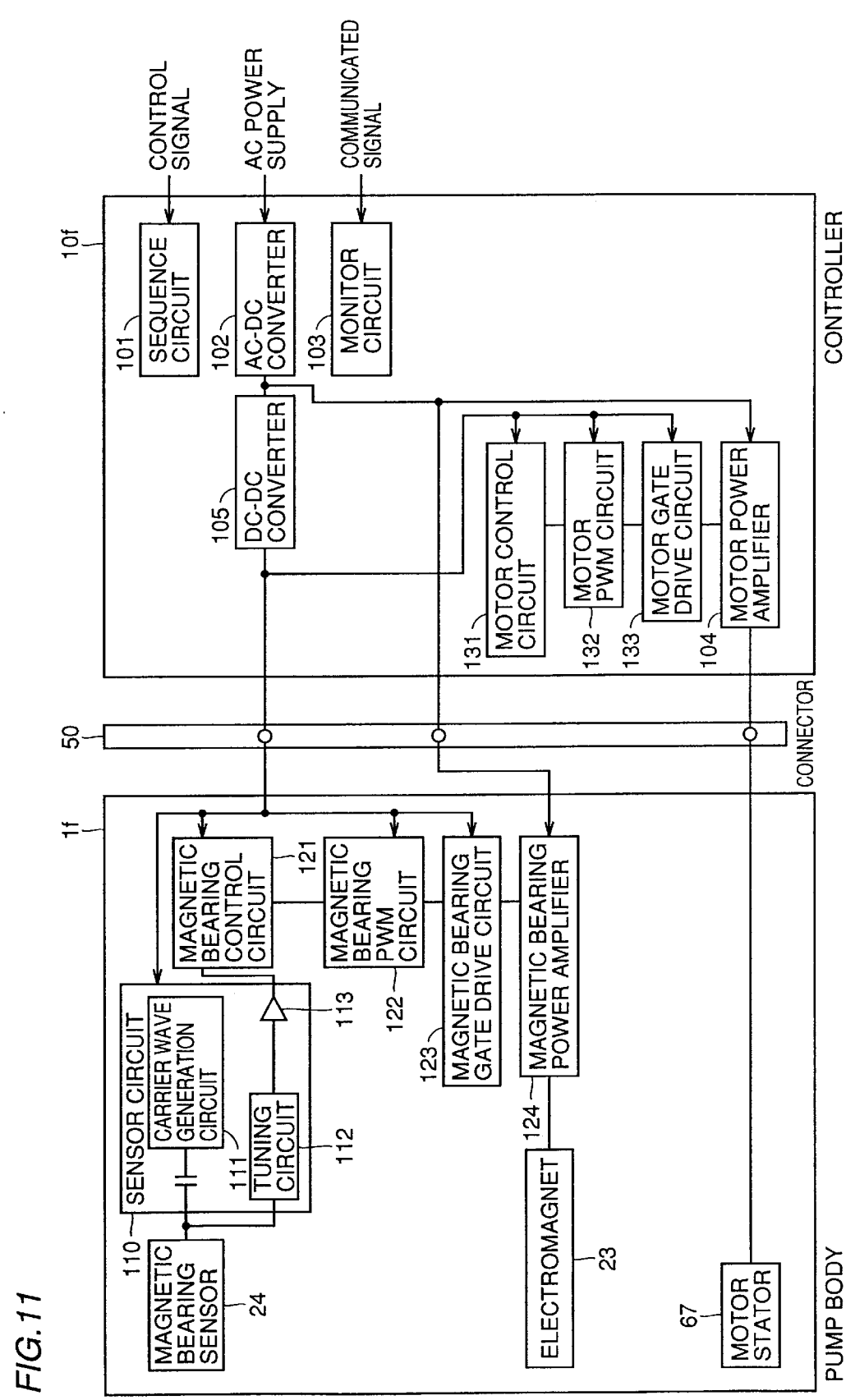

FIG. 11 is a block diagram showing a seventh embodiment of the controller in accordance with the present invention. In the present embodiment, sensor circuit 110 and the electromagnet 23 driving system are preferentially incorporated in a pump body 1f.

Figure 12:
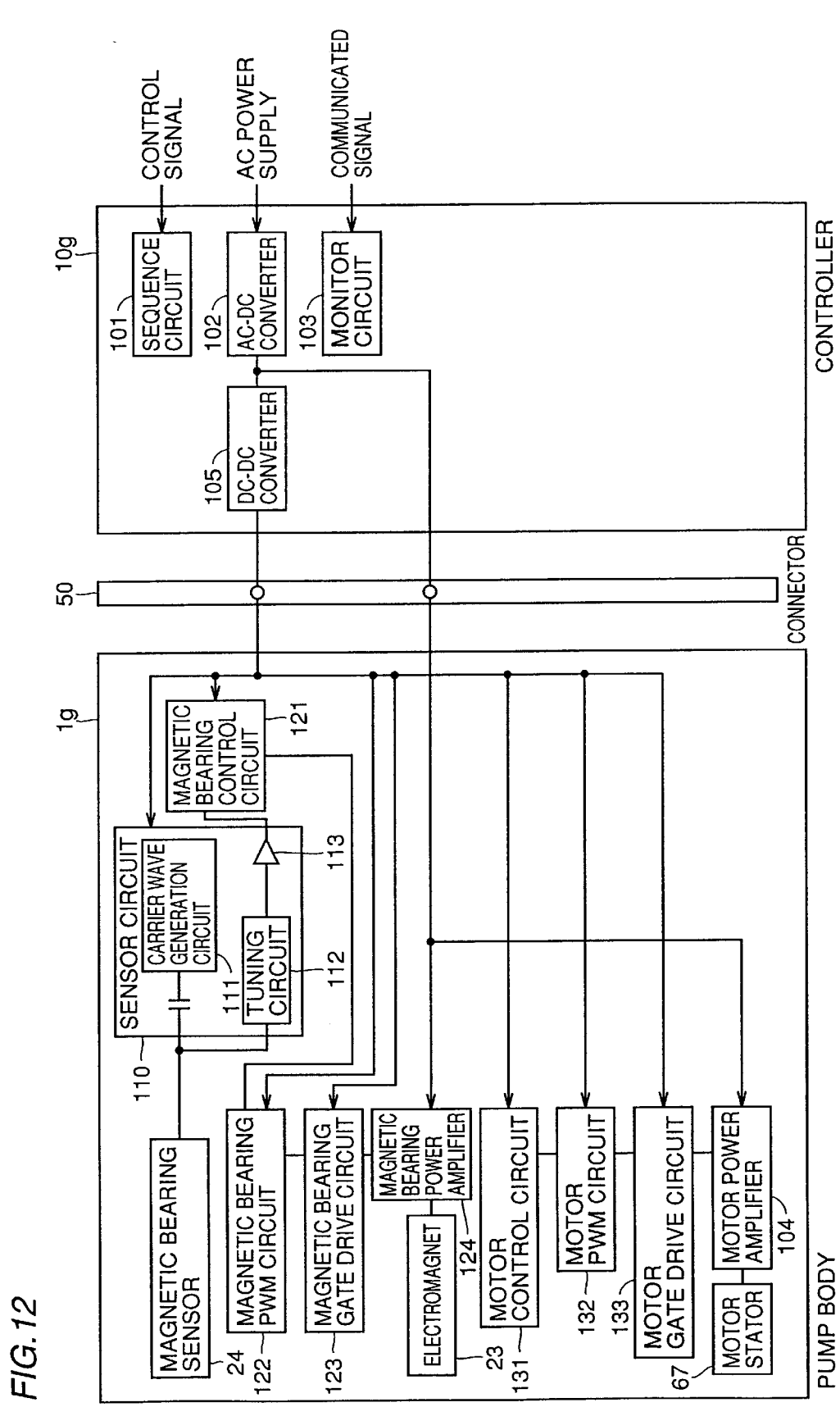

FIG. 12 is a block diagram showing an eighth embodiment of the controller in accordance with the present invention. In the present embodiment, sensor circuit 110, the electromagnet 23 and motor stator 67 driving systems are incorporated in a pump body 1g, and other circuits including a power supply circuit, a sequence circuit and a monitor circuit are incorporated in a controller 10g.

Figure 13:
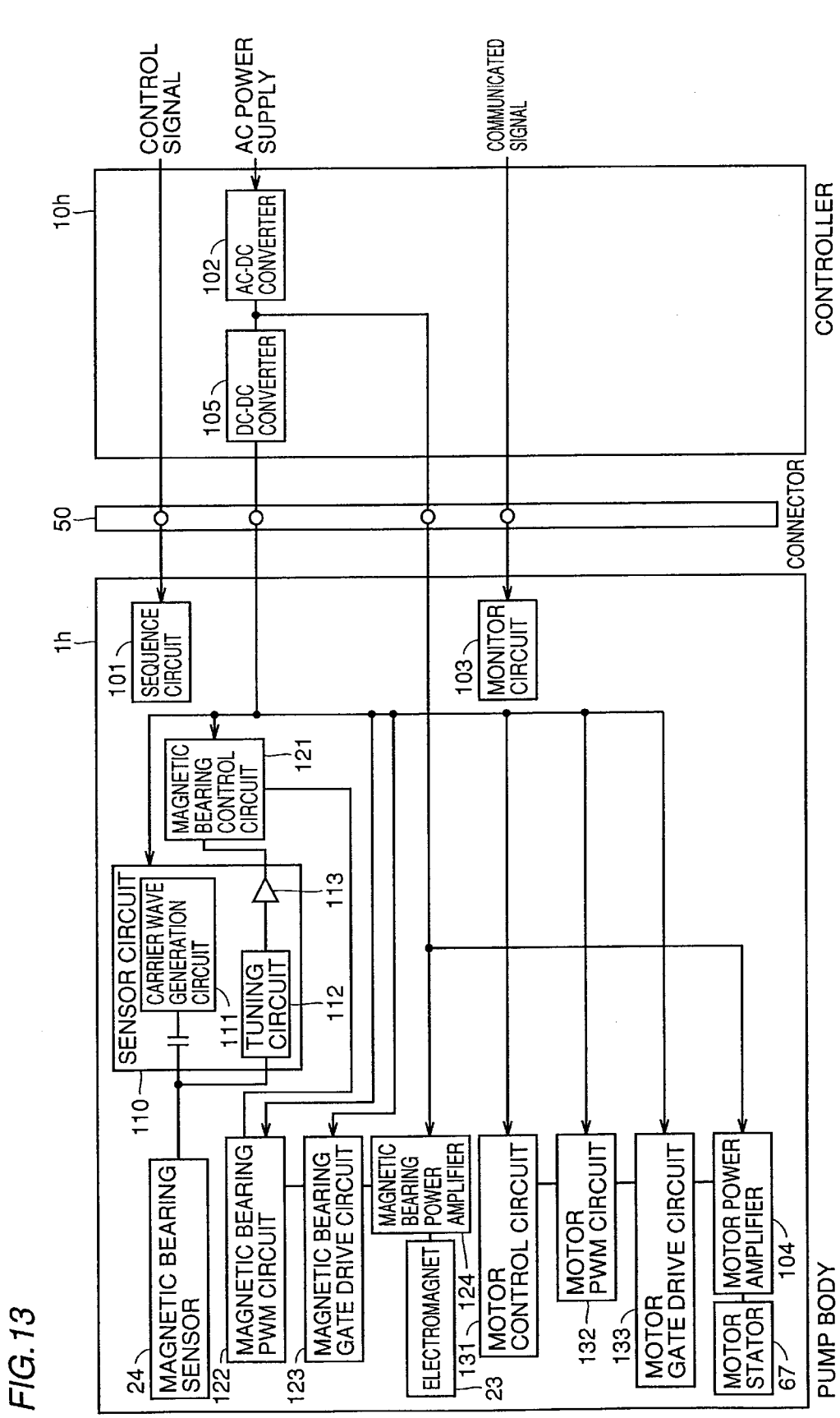

FIG. 13 is a block diagram showing a ninth embodiment of the controller in accordance with the present invention. A controller 10h only has incorporated therein AD-DC converter 102 and DC-DC converter 105, and pump body 1h has incorporated therein the remaining, sequence circuit 101, monitor circuit 103, sensor circuit 110, and the electromagnet 23 and motor stator 67 driving systems.

Figure 14:
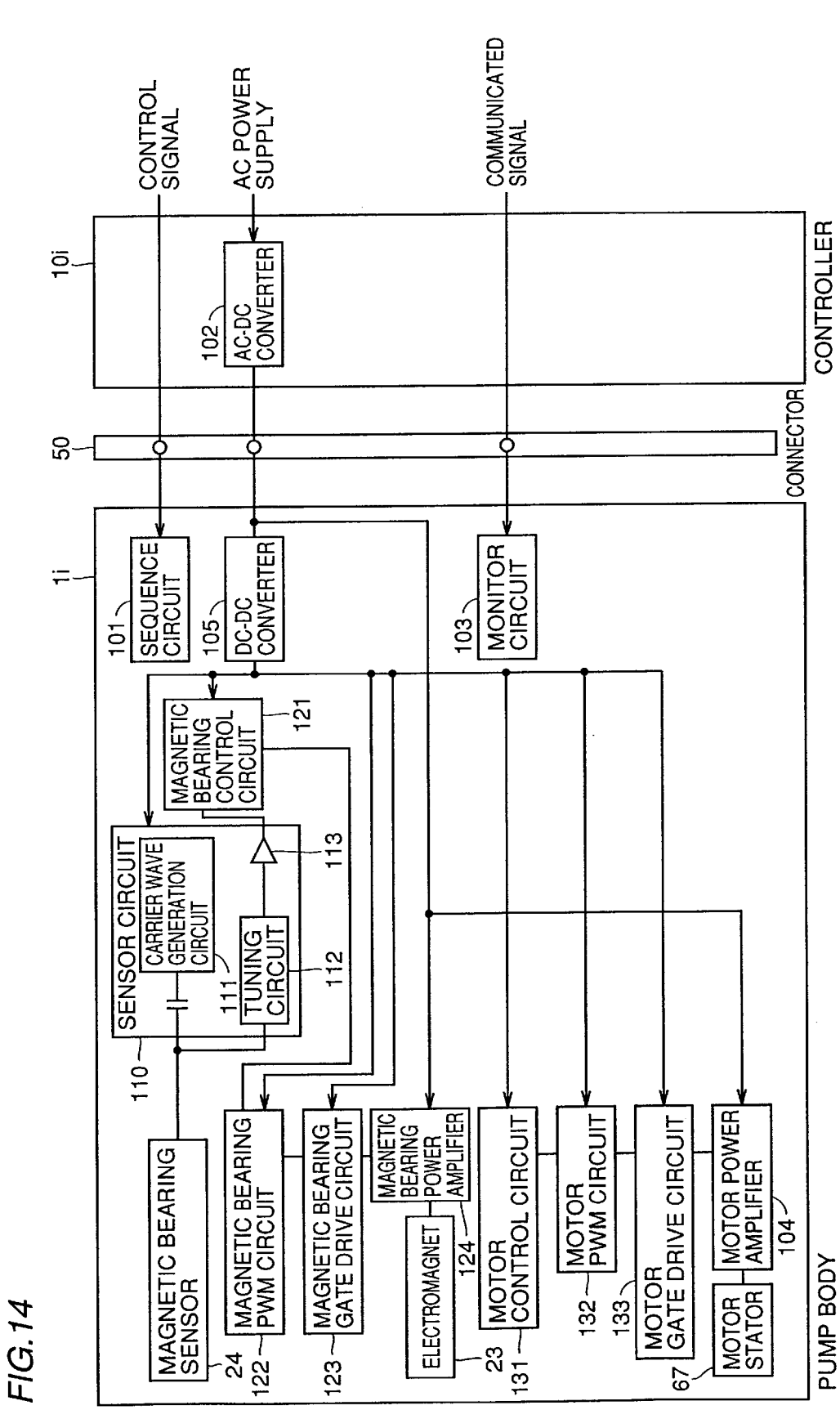

FIG. 14 is a block diagram showing a tenth embodiment of the controller in accordance with the present invention. In the present embodiment a controller 10i only has incorporated therein AC-DC converter 102 and a pump body 1i has incorporated therein all of the remaining components.

Although in the FIGS. 11–14 embodiments a pump body has a driving system incorporated therein and it is thus increased in size, the embodiments are advantageous as a satisfactory heat sink effect can be achieved and the pump body and the controller can have compatibility therebetween.

Thus in accordance with the embodiments of the present invention if a position detection circuit receiving a sensor output to determine the position of the impeller in levitation is housed in the casing the position detection circuit can have characteristics adjusted to correspond to the sensor of the body of the blood pump to maintain compatibility with the controller.

Furthermore, if any of a drive circuit controlling the drive means or a magnetic bearing control circuit controlling the controlled magnetic bearing unit is housed in the casing then heat generated from the drive circuit can be efficiently cooled by a fluid to prevent the controller body from generating significant heat.

Although the present invention has been described and illustrated in detail, it is clearly understood that the same is by way of illustration and example only and is not to be taken by way of limitation, the spirit and scope of the present invention being limited only by the terms of the appended claims.

What is claimed is:
1. A fluid pump apparatus comprising:
   a casing having therein
      a pump unit chamber,
      a drive unit chamber and
      a controlled magnetic bearing unit chamber;
   a pump unit being accommodated in said pump unit chamber and having a rotative member rotated to output a fluid;
   a drive unit accommodated in said drive unit chamber and coupled with one side of said rotative member contactless through a magnetic force to levitate said one side of said rotative member while rotatably driving said one side of said rotative member;
   a position detection unit being accommodated in said controlled magnetic bearing unit chamber and detecting a position of said rotative member in levitation; and
   a controlled magnetic bearing unit being accommodated in said controlled magnetic bearing unit chamber and contactlessly supporting the other side of said rotative member in response to an output of said position detection unit, wherein said casing includes a first partition provided between said pump unit chamber and said drive unit chamber to have these chambers partitioned from each other, and a second partition provided between said pump unit chamber and said controlled magnetic bearing unit chamber to have these chambers partitioned from each other, and said drive unit is attached to said first partition.

2. The fluid pump apparatus of claim 1, wherein: said controlled magnetic bearing unit is attached to said second partition.

3. The fluid pump apparatus of claim 1, wherein said position detection unit is attached to said second partition.

4. The fluid pump apparatus of claim 1, wherein:

said rotative member is formed in a disk having a side facing said drive unit and provided with a permanent magnet arranged circumferentially; and said rotative member and said drive unit are coupled contactless through magnetic-coupling.

5. The fluid pump apparatus of claim 4, wherein:

said rotative member is formed in a disk having a side facing said drive unit and provided with a first permanent magnet arranged circumferentially;

said drive unit is provided with a second permanent magnet arranged circumferentially to face said first permanent magnet; and said first and second permanent magnets provide magnetic-coupling to couple said rotative member and said drive unit together contactlessly.

6. The fluid pump apparatus of claim 2, wherein said controlled magnetic bearing unit includes a plurality of electromagnets each configured of a magnetic pole, a yoke and a coil and having an S magnetic pole and an N magnetic pole with at least said yoke and coil arranged circumferentially.

7. The fluid pump apparatus of claim 2, wherein said drive unit includes a motor stator and a motor rotor rotated by a magnetic force of said motor stator, said motor stator being attached to said second partition.

8. The fluid pump apparatus of claim 1, wherein said pump unit has an internal surface coated with heparin.

9. A fluid pump apparatus having a casing, an impeller driven, levitated, a drive unit driving said impeller, a sensor sensing a position of said impeller in levitation, and a controlled magnetic bearing unit contactlessly supporting said impeller in response to an output of said sensor, wherein said casing has housed therein at least one of a position detection circuit operative in response to the output of said sensor to determine the position of said impeller in levitation, a drive circuit controlling said drive unit, and a magnetic bearing control circuit controlling said controlled magnetic bearing.

10. The fluid pump apparatus of claim 9, further comprising:

an alternate current to direct current conversion circuit converting an alternate-current voltage to a direct-current voltage; and a direct current to direct current conversion circuit converting the direct-current voltage converted, into a different direct-current voltage, wherein said direct current to direct current conversion circuit is housed in said casing.

11. The fluid pump apparatus of claim 9, further comprising:

a carrier wave generation circuit generating a carrier wave; and a tuning circuit detecting a signal of said sensor tuned in to the carrier wave generated by said carrier wave generation circuit, to detect the position of said impeller in levitation, wherein said carrier wave generation circuit and said tuning circuit are housed in said casing.

12. A fluid pump apparatus comprising:

a casing having therein a pump unit chamber, a drive unit chamber and a controlled magnetic bearing unit chamber;

a pump unit being accommodated in said pump unit chamber and having a rotative member rotated to output a fluid;

a drive unit accommodated in said drive unit chamber and coupled with one side of said rotative member contactless through a magnetic force to levitate said one side of said rotative member while rotatably driving said one side of said rotative member;

a position detection unit being accommodated in said controlled magnetic bearing unit chamber and detecting a position of said rotative member in levitation; and a controlled magnetic bearing unit being accommodated in said controlled magnetic bearing unit chamber and contactlessly supporting the other side of said rotative member in response to an output of said position detection unit, wherein said casing includes a first partition provided between said pump unit chamber and said drive unit chamber to have these chambers partitioned from each other, and a second partition provided between said pump unit chamber and said controlled magnetic bearing unit chamber to have these chambers partitioned from each other, and said drive unit is attached to said first partition without contacting any other wall of said drive unit chamber.

13. The fluid pump apparatus of claim 12, wherein:

said controlled magnetic bearing unit is attached to said second partition without contacting any other wall of said controlled magnetic bearing unit chamber.

14. The fluid pump apparatus of claim 13, wherein:

said position detection unit is attached to said second partition without contacting any other wall of said controlled magnetic bearing unit chamber.

15. A fluid pump apparatus comprising:

a casing having therein a pump unit chamber, a drive unit chamber and a controlled magnetic bearing unit chamber;

a pump unit being accommodated in said pump unit chamber and having a rotative member rotated to output a fluid;

a drive unit accommodated in said drive unit chamber and coupled with one side of said rotative member contactless through a magnetic force to levitate said one side of said rotative member while rotatably driving said one side of said rotative member;

a position detection unit being accommodated in said controlled magnetic bearing unit chamber and detecting a position of said rotative member in levitation;

a controlled magnetic bearing unit being accommodated in said controlled magnetic bearing unit chamber and contactlessly supporting the other side of said rotative member in response to an output of said position detection unit, wherein said casing includes
- a first partition provided between said pump unit chamber and said drive unit chamber to have these chambers partitioned from each other, and
- a second partition provided between said pump unit chamber and said controlled magnetic bearing unit chamber to have these chambers partitioned from each other, and said drive unit is attached to said first partition without contacting any other wall of said drive unit chamber; and said casing has housed therein at least one of
- a position detection circuit operative in response to the output of said position detection unit to determine the position of said impeller in levitation,
- a drive circuit controlling said drive unit, and
- a magnetic bearing control circuit controlling said controlled magnetic bearing unit.

16. The fluid pump apparatus of claim 15, further comprising:

an alternate current to direct current conversion circuit converting an alternate-current voltage to a direct-current voltage; and a direct current to direct current conversion circuit converting the direct-current voltage converted, into a different direct-current voltage, wherein said direct current to direct current conversion circuit is housed in said casing.

17. The fluid pump apparatus of claim 15, further comprising:

a carrier wave generation circuit generating a carrier wave; and a tuning circuit detecting a signal of said sensor tuned in to the carrier wave generated by said carrier wave generation circuit, to detect the position of said impeller in levitation, wherein said carrier wave generation circuit and said tuning circuit are housed in said casing.

* * * * *